United States Patent [19]
Calmel

[11] Patent Number: 6,128,399
[45] Date of Patent: Oct. 3, 2000

[54] FINGERPRINT SENSOR DEVICE

[75] Inventor: Maryline Calmel, Chaville, France

[73] Assignee: Sagem SA, France

[21] Appl. No.: 08/952,452

[22] PCT Filed: Mar. 26, 1997

[86] PCT No.: PCT/FR97/00536

§ 371 Date: Nov. 20, 1997

§ 102(e) Date: Nov. 20, 1997

[87] PCT Pub. No.: WO97/36544

PCT Pub. Date: Oct. 9, 1997

[30] Foreign Application Priority Data

Mar. 28, 1996 [FR] France .................................. 96 03881

[51] Int. Cl.[7] ...................................................... G06K 9/00
[52] U.S. Cl. ......................... 382/124; 382/127; 382/126; 382/314; 382/315; 358/474; 358/483; 358/484
[58] Field of Search ..................................... 382/124, 127, 382/126, 312, 314, 315; 358/474, 483, 484

[56] References Cited

U.S. PATENT DOCUMENTS

| | | | |
|---|---|---|---|
| 4,394,773 | 7/1983 | Ruell | 340/146.3 |
| 5,050,220 | 9/1991 | Marsh et al. | 382/4 |
| 5,088,817 | 2/1992 | Igaki et al. | 356/71 |
| 5,325,442 | 6/1994 | Knapp | 355/40 |
| 5,448,649 | 9/1995 | Chen et al. | 382/4 |
| 5,544,338 | 8/1996 | Forslund | 395/400 |

*Primary Examiner*—Matthew Bella
*Assistant Examiner*—Sheela Chawan
*Attorney, Agent, or Firm*—Larson & Taylor, PLC

[57] ABSTRACT

The fingerprint sensor device comprises a thin flat transparent support (10) having an outside face for receiving the end of a finger and carrying on an inside face a two-dimensional matrix of photosensitive elements separated by strip-shaped gaps, and a substrate (14) carrying on an inside face light sources for directing light through the support via the strip-shaped gaps and substantially orthogonally to said outside face. The photosensitive elements are protected from the light coming from the sources so as to deliver an output signal only in response to light that has been back-scattered towards the outside face of the support.

11 Claims, 1 Drawing Sheet

FINGERPRINT SENSOR DEVICE

BACKGROUND OF THE INVENTION

The present invention relates to a fingerprint sensor device capable of detecting the ridges and furrows of a phalanx.

Such optical devices are already in existence, for example the device described in document FR-A-2 235 431, which devices make use of a two-dimensional array of detection sites associated with a recognition system.

SUMMARY OF THE INVENTION

It is an object of the invention to provide a fingerprint sensor device that satisfies practical requirements better than presently-known devices, particularly because of its simplicity and its suitability for distinguishing well between ridges and furrows, and thus for delivering a fingerprint with sharp lines.

To this end, the invention provides a fingerprint sensor device comprising:

- a thin flat transparent support having an outside face for receiving the end of a finger and carrying on an inside face a two-dimensional matrix of photosensitive elements which are distributed at a regular pitch of not more than 90 µm and which are separated by strip-forming transparent gaps that are generally of a width that is smaller than the width of the photosensitive elements;
- a substrate whose inside face, facing the support carries light sources for directing a light beam through the support via the gaps of the support and substantially orthogonally to said outside face; and
- means for lighting said sources and reading the photosensitive elements, said photosensitive elements being protected against the light coming from the sources so as to deliver an output signal only in response to light that has been back-scattered by the furrows towards the outside face of the support.

Each of the component elements of the device can be implemented in various different ways.

In advantageous embodiments, the sources are constituted by thin film light emitting diodes deposited on the inside face of the substrate, by parallel strips of light emitting diodes, or by a continuous flat component. By way of example, such a flat component may be formed by a plate of diffusing material such as acrylic resin, with the bottom face thereof carrying light emitting diodes that may be far fewer in number than the photosensitive elements, thereby reducing the cost of the device. The light emitting diodes (LEDs) may be stuck to the bottom face of the support, optionally in cavities provided for this purpose. The substrate may thus constitute a component which deflects or diffuses towards the support, light received from sources placed laterally or longitudinally relative thereto. The support which is a few millimeters thick can then be treated to constitute semitransparent micromirrors reflecting the light towards the gaps.

In general, the sources may be fixed on the outside face or on the inside face of the substrate or on one or more edges thereof.

The photosensitive elements may also be of various structures. They may be photodiodes integrated in a thin film of silicon belonging to the support or constituting the support. They may be thin film phototransistors, similar to those used in flat display screens. They may also be photo cells.

Usable sources that are available at low cost are specifically sources that emit in the visible range; in general, such sources are used together with photosensitive elements that are matched so as to present high sensitivity in the emission band of the source.

The above characteristics and others appear more clearly on reading the following description of a particular embodiment of the invention given by way of non-limiting example. The description refers to the accompanying drawing, in which.

DESCRIPTION OF THE EMBODIMENTS

The sensor device described by way of example is associated with a system for processing the resulting signals. The system may be of any of the types presently known, for example it may be of the type described in above-mentioned document FR-A-2 235 431, to which reference may be made.

Figure 1:
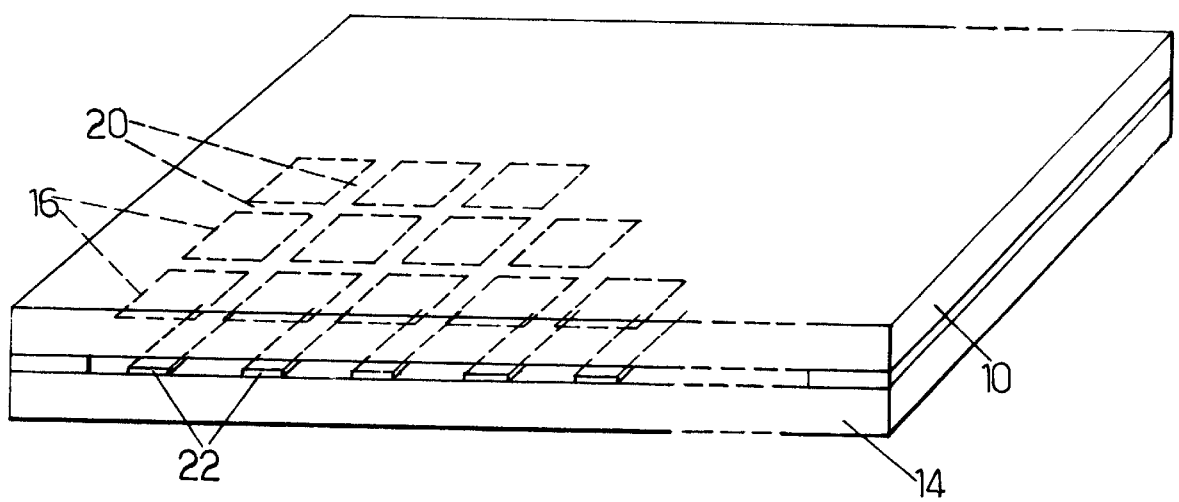
FIG. 1 is an overall perspective view showing one possible structure for a sensor device.

The sensor device shown diagrammatically in FIG. 1 can be considered as comprising a transparent support 10 on which a finger 12 is pressed in order to obtain a fingerprint, together with a substrate 14 which is fixed to the support 10.

The inside face of the support 10 carries a two-dimensional matrix of photosensitive elements 16, of which only a few are shown in FIG. 1. These photosensitive elements are protected against light coming from the substrate (arrow f in FIG. 2), e.g. by an opaque deposit 18. The deposit may be of metal. It must be thick enough to transmit practically no light. The deposit may be reflective, thereby making it possible to reduce light losses.

As mentioned above, the photosensitive elements are separated by gaps 20 through which light passes.

The photosensitive elements 16 may be of any of the structures commonly used at present when they should be thin. In particular, it is possible to use thin film photodiodes or phototransistors made on a transparent support 10, usually of glass or of quartz.

The pitch at which the elements 16 are distributed i.e. their mutual spacing, must be smaller than the distance between two successive furrows in a fingerprint. In practice, this pitch must not exceed 80 µm. The pitch can be considerably smaller, however no increase in selectivity is obtained by going to less than 50 µm, as a consequence the distribution pitch selected will generally lie in the range 50 µm to 80 µm.

The output signals from the photosensitive elements are taken out from the sensor device by narrow tracks made in a manner that is conventional in thin film technology.

In particular, the photosensitive elements may be in a matrix disposition for row by row scanning. Under such circumstances, each photosensitive element comprises a light detection zone constituting a particular pixel and associated with a driver circuit, such as a thin film transistor connected both to a column conductor and to a row conductor. The thin film transistors may be similar to those now currently used in LCD displays. The column conductors and row conductors are connected to read-out electronics. The conductors and the interconnections can be constituted by narrow tracks that are sufficiently narrow to be transparent, or they may even be opaque if they are narrow, e.g. being made of gold.

The sensor device also includes means for transmitting light from the substrate towards the sensor, which light passes through the gaps in a direction that is as nearly orthogonal as possible to the support.

In the example shown in FIG. 1, these means are constituted by light emitting strips 22, thus making it easier to power them electrically. They may be constituted, in particular, by LEDs of the kind used in facsimile receivers and they can be deposited in thin layers on the substrate. The LEDs are chosen to correspond to the sensitivity peak of the photosensitive elements, i.e. generally at a wavelength of about 650 nanometers. It is even possible to use parallel strips.

In another embodiment, the sources are constituted by individual LEDs, each placed at a cross-point between two gaps. Each of the diodes may carry a lens for concentrating the emitted light flux, thereby providing an emission lobe that is as narrow as possible and as directional as possible towards the support. The light emitting means may also be constituted by a single component covering the inside face of the substrate 14, and having zones that can be masked so that light is emitted only from portions situated facing the gaps or the gap cross-points. Masking may be performed by silk-screening, painting, depositing a reflecting layer, or bonding an opaque adhesive strip.

It is also possible to use a diffusing support which receives light from emitters fixed on its edge or on its back face. In this case also, a mask may be provided on the inside face of the substrate.

Figure 2:
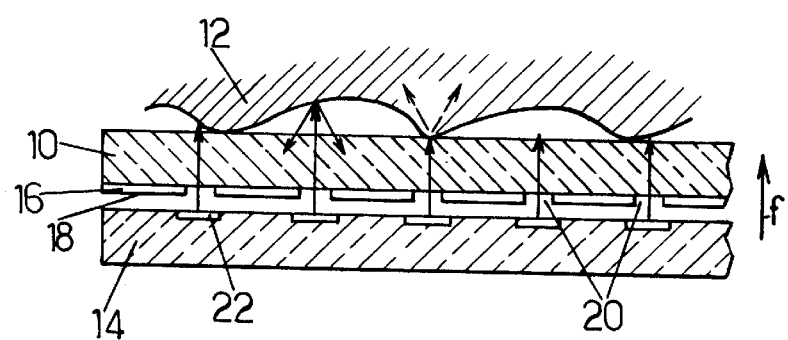
FIG. 2 is a diagrammatic section view for showing how ridges and furrows are distinguished when the sensor is taking a fingerprint.

The mode of operation of the sensor device can be seen in FIG. 2. Incident light penetrating into a furrow or valley is scattered by the furrow and some of it returns towards one or more photosensitive elements. In contrast, incident light striking a ridge in contact with the support is absorbed by the finger. The facing sensitive elements receive practically no light. The read means (not shown) associated with the photosensitive elements can be designed to compare the voltage or the current delivered by each element with a threshold so as to make the distinction.

The sensor device described above provides a direct representation of a fingerprint at life size, and that is an advantage from the point of view of processing. The sensor device can be made using miniaturization technologies that are now thoroughly mastered.

What is claimed is:

1. A fingerprint sensor device, comprising:

at transparent support having an outside face for contact with an end portion of a finger and an inside face carrying a two-dimensional array of photosensitive elements distributed at a regular spacing at most equal to 90 μm, the photosensitive elements being separated by transparent strip-shaped gaps having a width that is smaller than an individual width of the photosensitive elements;

a substrate fixed relative to the support, having an inside face confronting the support and parallel thereto and carrying light source means for directing light beams through the support via the strip-shaped gaps of the support, in a direction substantially orthogonal to said outside face;

means for energizing said light source means and for reading-out the photosensitive elements; and means for protecting said photosensitive elements against light directly coming from said light source means;

whereby an output signal of said photosensitive elements is only responsive to light leaving said support through said outside face and back-scattered towards said outside face of the support.

2. A device according to claim 1, characterized in that the sources are constituted by thin-film light-emitting diodes deposited on the substrate, parallel strips of light emitting diodes, or a continuous flat component.

3. A device according to claim 1, characterized in that the sources are constituted by individual light emitting diodes, each carrying a lens for concentrating its emitted light flux.

4. A device according to claim 1, characterized in that the photosensitive elements are constituted by photodiodes integrated in a thin film of silicon constituting the support.

5. A device according to claim 4, wherein said sources emit near infrared or visible light.

6. A device according to claim 1, characterized in that the photosensitive elements are photocells or thin film phototransistors.

7. A device according to claim 1, characterized in that the gaps are of a width that is smaller than the width of the photosensitive elements.

8. A device according to claim 1, characterized in that the substrate is a component for deflecting towards the support light received from sources placed laterally or longitudinally relative to the substrate.

9. A fingerprint sensor device, comprising:

a flat transparent support having a flat outside face designed to receive the end of a finger and carrying, on an inside face thereof, a two-dimensional array of photosensitive elements distributed at a regular spacing and separated by transparent gaps of width that is smaller that of the photosensitive elements;

a substrate fixed relative to the support, having an inside face confronting the inside face of the support;

light source means for directing light beams from the inside face of the substrate to and through the support, via the gaps on the support, substantially orthogonally to said outside face;

means for energizing said sources and for reading out the photosensitive elements; and protection means for protecting said photosensitive elements against light directly coming from said light sources so as to provide an output signal only in response to light back-scattered from the flat outside face towards the outside face of the support.

10. A device according to claim 9, characterized in that the substrate carries sources on an external face or on an internal face directed towards the support.

11. A device according to claim 9, wherein said protection means comprise an opaque coating on said photosensitive elements.

* * * * *